(12) United States Patent
Bahls et al.

(10) Patent No.: US 9,820,640 B2
(45) Date of Patent: Nov. 21, 2017

(54) CAMERA SYSTEM AND METHOD FOR CLEANING A CAMERA

(71) Applicant: Deutsches Zentrum Fur Luft-und Raumfahrt E.V., Cologne (DE)

(72) Inventors: Thomas Bahls, Weil (DE); Florian Alexander Froehlich, Germering (DE)

(73) Assignee: DEUTSCHES ZENTRUM FUER LUFT-UND RAUMFAHRT E.V., Cologne (DE)

(*) Notice: Subject to any disclaimer, the term of this patent is extended or adjusted under 35 U.S.C. 154(b) by 314 days.

(21) Appl. No.: 14/610,532

(22) Filed: Jan. 30, 2015

(65) Prior Publication Data

US 2015/0216401 A1 Aug. 6, 2015

(30) Foreign Application Priority Data

Feb. 5, 2014 (DE) .................. 10 2014 202 075

(51) Int. Cl.
| | |
|---|---|
| *A61B 1/12* | (2006.01) |
| *A61B 1/00* | (2006.01) |
| *A61B 1/05* | (2006.01) |
| *A61B 1/313* | (2006.01) |
| *G02B 27/00* | (2006.01) |
| *G02B 23/24* | (2006.01) |
| *A61B 90/70* | (2016.01) |

(52) U.S. Cl.
CPC .......... *A61B 1/126* (2013.01); *A61B 1/00096* (2013.01); *A61B 1/00135* (2013.01); *A61B 1/00142* (2013.01); *A61B 1/05* (2013.01); *A61B 1/127* (2013.01); *A61B 1/3132* (2013.01); *G02B 23/2484* (2013.01); *G02B 27/0006* (2013.01); *A61B 2090/701* (2016.02)

(58) Field of Classification Search
CPC ......... A61B 1/126; A61B 1/05; A61B 1/3132; A61B 1/00096; A61B 1/00135; A61B 1/00101; A61B 1/00142; A61B 1/00144; A61B 1/127; G02B 23/2484
See application file for complete search history.

(56) References Cited

U.S. PATENT DOCUMENTS

| | | | |
|---|---|---|---|
| 5,363,843 | A | 11/1994 | Daneshvar |
| 5,518,502 | A | 5/1996 | Kaplan et al. |
| 5,575,756 | A | 11/1996 | Karasawa et al. |
| 6,009,971 | A | 1/2000 | Weidman et al. |
| 6,254,386 | B1 | 7/2001 | Ohmes |
| 6,755,782 | B2 | 6/2004 | Ogawa |
| 2010/0174144 | A1 | 7/2010 | Hsu et al. |
| 2010/0249503 | A1 | 9/2010 | Yazawa et al. |
| 2012/0092765 | A1 | 4/2012 | Kline et al. |
| 2012/0101338 | A1 | 4/2012 | O'Prey et al. |

(Continued)

FOREIGN PATENT DOCUMENTS

| | | |
|---|---|---|
| EP | 2443986 A1 | 4/2012 |
| JP | 200505229 A | 3/2005 |
| WO | 2014048972 A1 | 4/2014 |

*Primary Examiner* — Timothy J Neal
(74) *Attorney, Agent, or Firm* — Ohlandt, Greeley, Ruggiero & Perle, LLP

(57) ABSTRACT

A camera system, particularly for minimally-invasive surgery, comprising an optics, wherein the optics is connected to at least one transparent film and the film is removable. Further, there is provided a method for cleaning a camera in minimally-invasive surgery wherein an optics of the camera is cleaned intracorporally by use of a cleaning device.

14 Claims, 1 Drawing Sheet

(56) References Cited

U.S. PATENT DOCUMENTS

2012/0108904 A1    5/2012  Ma et al.
2012/0178995 A1    7/2012  Newton, IV
2012/0238818 A1    9/2012  O'Prey et al.

CAMERA SYSTEM AND METHOD FOR CLEANING A CAMERA

RELATED CROSS-REFERENCING

The present disclosure claims the priority of German Patent Application DE 10 2014 202 075.1 filed on Feb. 5, 2014, the disclosure of which is incorporated herein by reference.

BACKGROUND

1. Field of the Disclosure

The present disclosure relates to a camera system, particularly for minimally-invasive surgery, and a method for cleaning a camera for minimally-invasive surgery.

2. Discussion of the Background Art

In minimally-invasive surgery, special instruments and optics are introduced into the patient via working trocars. For this purpose, merely small incisions will have to be made in the skin. The advantages of minimally-invasive surgery reside e.g. in reduced scars, faster convalescence, reduced risk of infection and briefer stays in hospital.

As compared to open surgery, operations of the minimally-invasive type often require longer operation times. For this reason, it is important to minimize the number of instances where instruments are changed. Apart from the temporal aspect, the changing of instruments will each time cause an interruption of the workflow performed by the surgeon. In addition to the actual changing of instruments, it is required, depending on the type of operation, to clean the optics at regular intervals because these may become fogged or be soiled by body liquids. To this end, the optics has to be removed from the patient's body, be cleaned and be introduced again. As stated by physicians, this has to be performed at intervals of about 10 minutes. In case of longer operations, this can lead to up to 20 to 30 cleaning cycles.

It is an object of the disclosure to provide to provided a camera system and a method, particularly for minimally-invasive surgery, wherein the cleaning of a camera is simplified.

SUMMARY

The camera system of the disclosure comprises a camera with optics. Particularly, the camera is suited for minimally-invasive surgery so that the optics preferably is of the endoscopic type. Particularly, the optics comprises at least one surface which in conventional cameras is subjected to the influence of the ambience. By means of the optics, images of the operation situs are transmitted to a monitoring device. The respective concrete realization of the transmission and of the monitoring device is not relevant for the disclosure.

According to the disclosure, the optics has connected to it at least one transparent film, wherein said film is removable. Particularly, the film is connected to said at least one surface. Preferably, at least one film is connected directly to said at least one surface. By removing the film, also contamination depositing on the optics and obstructing the same while causing the image quality to deteriorate, will be removed from the optics along with the film. The film is transparent to visible light, i.e. it has low intrinsic absorption for visible light. Alternatively or additionally thereto, however, the film can also be transparent in the infrared range.

Preferably, the film covers said at least one surface of the optics entirely.

Particularly, the transparent film can be a film made of plastic. If it is desired to remove the transparent film from the optics intracorporally, the transparent film, in case it is a plastic film, has to be removed from the body either by suctioning or by guiding it away from the operation situs, and preferably it is guided out of the body. By way of alternative thereto, the transparent film can also be made of a biocompatible material such as e.g. gelatin so that, after having been removed from the optics, the transparent film can be left in the body and will be resorbed by the body.

Particularly, the film can be removed from the optics without leaving residues. Removal is performed particularly by peeling off the film. In order to allow for a residue-free removal of the film from the optics, the film can comprise a releasable adhesive layer connecting the film with the optics and particularly with said at least one surface of the optics. By way of alternative thereto, the connection of the optics with the film can be effected by Van-Der-Waals force and by adhesion, respectively.

Preferably, the optics is connected to a plurality of mutually superposed films. In such an arrangement, the films are preferably removable individually. Particularly, the optics and said at least one surface are covered by the plurality of mutually superposed films over their full surface area. The provision of a plurality of mutually superposed films makes it possible to clean the optics of the camera a plurality of times by successively removing individual transparent films wherein, with each removal of an individual film, also contamination obscuring the optics will be removed together with the film. Preferably, for cleaning, the last film when viewed from the optics of the camera will be removed.

Preferably, the film comprises a plurality of portions wherein a top side of a portion is preferably connected to an immediately preceding portion, and a bottom side of the portion with a directly following portion. A first portion is preferably connected to the optics. The individual portions are folded onto each other in such a manner that they are arranged in a meandering configuration. Particularly, the optics is cleaned by removing the respective last portion from the immediately preceding portion. Thus, multiple cleaning of the optics is possible in dependence on the number of the provided portions.

Preferably, the connection of the individual portions is releasable. For this purpose, an adhesive layer, which then of course has to be transparent, can be arranged between the individual portions, or the connection of the individual portions can be realized by adhesion.

Preferably, at least one film comprises a flap for facilitating removal. Said flap can be gripped more easily. This is of eminent advantage particularly in minimally-invasive surgery since, in this type of surgical intervention, removal of the film is performed intracorporally with the aid of an endoscopic instrument. In this regard, it is particularly preferred if the flaps are arranged with mutual displacement along the periphery of the film. Thereby, the flaps do not overlap each other, thus making it still easier to grip an individual flap.

Preferably, there is provided a removal device for removal of the transparent film. Said removal device is preferably designed as a gripping device which can be a separate instrument, again of an endoscopic type.

With particular preference, however, the removal device is connected to the camera. In this manner, only one instrument is required. Particularly, the removal device is designed in such a manner that, if a film comprises a plurality of portions, the individual portions of the film can be successively released from each other by pulling a flap that is preferably provided.

The disclosure further relates to a method for cleaning a camera system in minimally-invasive surgery, said camera system comprising a camera. In the method of the disclosure, the optics of a camera is cleaned intracorporally by use of a cleaning device. Thereby, it is not required anymore to remove the optics from the patient's body and to clean the optics externally. This allows for a considerable reduction of time required for the surgical operation.

Particularly, the cleaning device is arranged on an instrument and the camera on another instrument, wherein, for cleaning the optics, the cleaning device will be advanced to the optics and the optics will then be cleaned. Alternatively, the cleaning device can also be used for intracorporal cleaning of endoscopic instruments. For instance, in minimally-invasive robotic surgery, the position of each robot is known from the kinematics. The distance between the various robots is likewise known. (This can be determined both by the design and by a tracking system.) On the basis of this information, the optics which is held by a robot can be approached by an additional robot closely enough to allow for a cleaning process to be performed within the patient's body. By way of alternative thereto, the cleaning device can also be approached to the optics manually.

Preferably, the cleaning device is arranged on an instrument comprising the camera.

Particularly, cleaning the optics can be performed by rinsing and/or blowing and/or stripping by the cleaning device.

Preferably, the optics is connected to at least one film, wherein the optics will be cleaned by removing the film. By removing the film, also the contamination obscuring the optics will be removed.

Preferably, the optics is connected to a plurality of films so that the optics can be cleaned a plurality of times by removing of individual films.

Preferably, the film comprises a plurality of portions, wherein the individual portions are folded onto each other and the optics will be cleaned by releasing a portion from the immediately preceding portion. Particularly, a first portion is connected directly with the optics. Along with the released portion, also the contamination obscuring the optics will be removed.

Preferably, two successive portions are connected to each other by a releasable adhesive layer.

Preferably, said at least one film comprises a flap. Thereby, particularly, removal of the film is facilitated. It is particularly preferred that the film comprises a plurality of portions, wherein the respective last portion can be released by pulling the flap. Particularly, by continuously pulling the flap, all portions will be released successively. With each removal of a portion, a cleaning process will be performed on the optics.

Particularly, the cleaning device is designed as a removal device for removing the film.

Particularly, said method is designed in accordance with the above described device features.

BRIEF DESCRIPTION OF THE DRAWINGS

A full and enabling disclosure of the present disclosure, including the best mode thereof, enabling one of ordinary skill in the art to carry out the disclosure, is set forth in greater detail in the following description, including reference to the accompanying drawing in which.

DETAILED DESCRIPTION OF THE PREFERRED EMBODIMENT

Figure 1:
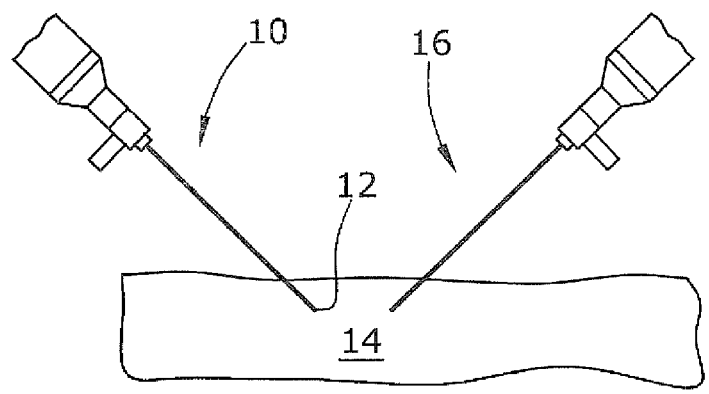
FIG. 1 is a schematic representation of the camera system of the disclosure.

The camera system of the disclosure comprises a camera 10 with optics 12, wherein at least one surface of the optics 12 is subjected to influences from the ambience and particularly may be contaminated thereby. The camera 10 is designed as an endoscopic camera for minimally-invasive surgery. In FIG. 1, camera 10 is provided for monitoring the operation situs 14. According to the method of the disclosure, a cleaning device 16, likewise designed as a surgical instrument for minimally-invasive surgery, can be approached to the optics 12. Subsequently, possibly existing contamination on the optics 12 can be rinsed off, blown off or stripped off by the cleaning device 16. This method is particularly useful if the camera 10 as well as the cleaning device 16 are guided in a robot-based manner, particularly with the aid of a surgical robot. In this case, the position of the optics 12 of camera 10 is sufficiently known so that the cleaning device 16 can be advanced to the optics 12 in a precise manner.

Figure 2:
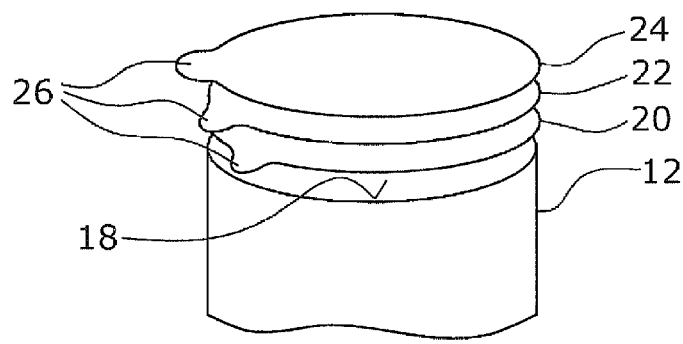
FIG. 2 is a detailed view of the optics of the camera system of the disclosure comprising a plurality of films illustrated in exploded view.
Figure 3:
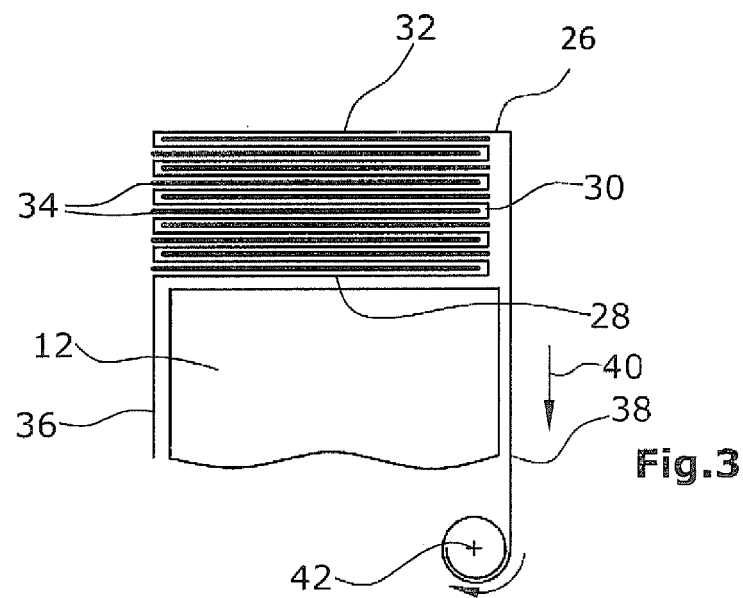
FIG. 3 is a detailed view of an optics of the camera system of the disclosure comprising a film arranged in meandering configuration.

FIG. 2 is an exploded detailed view of an optics 12. Optics 12 comprises a surface 18 fully covered by at least one transparent film 20. In FIG. 3, three transparent films 20, 22, 24 are shown. In this arrangement, said films 20, 22, 24 are situated above each other and fully cover said surface 18 of optics 12. Further, said films 20, 22, 24 comprise flaps 26. These flaps 26 are arranged with mutual displacement along the periphery of the films. Thereby, gripping the flaps is facilitated and, in a corresponding manner, also removing the associated films is facilitated.

The first film 20 is directly connected to the surface 18 of the optics 12. For cleaning the optics 12, the respective last film 24 will be released by pulling it off. Contamination on film 24 will be removed from the optics together with the film.

A film (FIG. 3) connected to the optics 12 can comprise a plurality of portions 30, wherein these portions 30 are arranged in a meandering configuration. In this arrangement, the film comprises a first portion 28 which particularly is connected directly to the optics 12. Further, the film comprises a last portion 32. The individual portions are connected to each other by adhesive layers 34. Further, the film comprises a holding flap 36 ensuring a better connection of film 26 to the optics 12. Still further, the film comprises a pull-off flap 38. By pulling said pull-off flap 38 in the direction marked by arrow 40, the last portion 32 of the film will be released from the preceding portion. Continuously pulling the pull-off flap 38 along arrow 40 has the effect that all portions, from said last portion 32 to said first portion 28, will be successively released from each other. This makes it possible to clean the optics 12 and remove contamination a plurality of times. Particularly, the individual portions will be released with the aid of a removal device 42 which is operative e.g. to wind up the film and which, as a result of the wind-up process, will be pulled on the pull-off flap 38 along arrow 40.

Although the disclosure has been described and illustrated with reference to specific illustrative embodiments thereof, it is not intended that the disclosure be limited to those illustrative embodiments. Those skilled in the art will recognize that variations and modifications can be made without departing from the true scope of the disclosure as defined by the claims that follow. It is therefore intended to include within the disclosure all such variations and modifications as fall within the scope of the appended claims and equivalents thereof.

What is claimed is:

1. A camera system for minimally-invasive surgery, comprising:
   a camera comprising an optics, wherein the optics is connected to at least one transparent film and the at least one transparent film is removable, wherein the at least one transparent film comprises a plurality of portions that have been folded onto each other in a meandering configuration.

2. The camera system according to claim 1, wherein the at least one transparent film comprises a plurality of mutually superposed films.

3. The camera system according to claim 1, wherein a top side of one portion is connected to an immediately preceding portion, and a bottom side of the one portion is connected to a directly following portion.

4. The camera system according to claim 3, wherein the plurality of portions are releasably connected to one another by an adhesive layer arranged between the plurality of portions.

5. The camera system according to claim 1, wherein the at least one transparent film comprises a flap.

6. The camera system according to claim 1, wherein the at least one transparent film comprises a removal device provided for removal of the at least one transparent film from the optics.

7. The camera system according to claim 6, wherein the removal device is connected to the camera.

8. A method for cleaning the camera according to claim 1, comprising cleaning the optics of the camera intracorporeally by removing one portion of the at least one transparent film from the optics.

9. The method according to claim 8, wherein the step of cleaning the optics further comprises rinsing and/or blowing the at least one transparent film.

10. The method according to claim 8, wherein the at least one transparent film comprises a flap.

11. The method according to claim 8, wherein the cleaning step comprises releasing a portion of the plurality of portions from an immediately preceding portion of the plurality of portions.

12. The method according to claim 11, wherein the cleaning step comprises releasing a respective last portion of the plurality of portions by pulling a flap.

13. The method according to claim 12, wherein, by continuously pulling the flap, all of the plurality of portions are released successively.

14. The camera system according to claim 1, wherein the camera is an endoscopic camera.

* * * * *